(12) United States Patent
Choi et al.

(10) Patent No.: US 9,206,165 B2
(45) Date of Patent: Dec. 8, 2015

(54) TETRAZOLO HYDRAZINE DERIVATIVES AND PHARMACEUTICAL COMPOSITION COMPRISING SAME AS ACTIVE INGREDIENT FOR PREVENTING OR TREATING CANCER

(71) Applicant: INDUSTRY-ACADEMIC COOPERATION FOUNDATION, YEUNGNAM UNIVERSITY, Gyeongsan-si (KR)

(72) Inventors: In Ho Choi, Gyeongsan-si (KR); Athar Fareeda, New Delhi (IN); Roouf Bhat Abdul, New Delhi (IN)

(73) Assignee: INDUSTRY-ACADEMIC COOPERATION FOUNDATION, YEUNGNAM UNIVERSITY (KR)

( * ) Notice: Subject to any disclaimer, the term of this patent is extended or adjusted under 35 U.S.C. 154(b) by 0 days.

(21) Appl. No.: 14/419,531

(22) PCT Filed: Aug. 6, 2013

(86) PCT No.: PCT/KR2013/007083
§ 371 (c)(1),
(2) Date: Jun. 22, 2015

(87) PCT Pub. No.: WO2014/025191
PCT Pub. Date: Feb. 13, 2014

(65) Prior Publication Data
US 2015/0291566 A1     Oct. 15, 2015

(30) Foreign Application Priority Data

Aug. 6, 2012   (KR) .................. 10-2012-0085947

(51) Int. Cl.
*C07D 405/04* (2006.01)
*A61K 31/41* (2006.01)

(52) U.S. Cl.
CPC .................................... *C07D 405/04* (2013.01)

(58) Field of Classification Search
None
See application file for complete search history.

(56) References Cited

U.S. PATENT DOCUMENTS

2004/0186295 A1   9/2004   Cosford et al.
2008/0206320 A1   8/2008   Michelet et al.

OTHER PUBLICATIONS

International Search Report—PCT/KR2013/007083 dated Nov. 13, 2013.
Mohmmad Y. Wani et al., Probing the antiamoebic and cytotoxicity potency of novel tetrazole and triazine derivatives, European Journal of Medicinal Chemistry, 2012, pp. 313-320.
Daniel R. Rhodes et al., AGTR1 overexpression defines a subset of breast cancer and confers sensitivity to losartan, an AGTR1 antagonist, PNAS, 2009, pp. 10284-10289.

*Primary Examiner* — Alicia L Otton
(74) *Attorney, Agent, or Firm* — Cantor Colburn LLP

(57) ABSTRACT

Provided are novel tetrazolo hydrazone derivatives or pharmaceutically acceptable salts thereof. The derivatives and the salts may inhibit the proliferation of cancer cells in a low molar concentration and inhibit the activity of cancer cells through the regulation of expression of apoptosis-related genes or the like, thus expressing excellent anti-cancer activity, and therefore, can be used effectively in preventing or treating cancer.

9 Claims, 5 Drawing Sheets

TETRAZOLO HYDRAZINE DERIVATIVES AND PHARMACEUTICAL COMPOSITION COMPRISING SAME AS ACTIVE INGREDIENT FOR PREVENTING OR TREATING CANCER

TECHNICAL FIELD

The present invention relates to novel tetrazolo hydrazone derivatives or pharmaceutically acceptable salts thereof, and to a pharmaceutical composition for preventing or treating cancer comprising the same as an active ingredient.

BACKGROUND ART

Cancer is a major cause of death in the world. Despite of numerous efforts trying to figure out new approach for cancer treatment, the range of choice in initial treatment is confined to alone or a combination of surgery, chemotherapy and radiation therapy. However, the surgery and radiation therapy are useful only in clearly identified types of cancer, its use for treating a patient having already spread disease is limited.

Chemotherapy is a useful method for treating a patient who suffers from metastatic cancer or diffuse cancer such as leukemia. Even though chemotherapy can provide a therapeutic effect, the chemotherapy may often end in failure because the patient's cancer cells may have a resistance to the chemotherapeutic agent. Therefore, the chemotherapeutic agent is typically provided in combination with other agent, because surroundings of the cancer cells may have a resistance to the chemotherapeutic agent.

Therefore, another chemical treatment method and chemotherapeutic agent are required, and in order to find the chemotherapeutic agent for the treatment of cancer, researchers, academia and companies are making constant efforts. In particular, heterocycle compounds are widely used for the treatment of cancer, many researches are concentrated on compounds with tetrazole ring, and many biologically active materials have been reported (Rhodes D R, Ateeq B, Cao Q, Tomlins S A, Mehra R, Laxman B, Kalyana-Sundaram S, Lonigro R J, Helgeson B E, Bhojani M S, Rehemtulla A, Kleer C G, Hayes D F, Lucas P C, Varambally S, Chinnaiyan A M. AGTR1 overexpression defines a subset of breast cancer and confers sensitivity to losartan, an AGTR1 antagonist. PNAS 2009/10.1073/pnas.0900351106). Particularly, 5-substituted 1,2,3,4-tetrazole was reported to have antibacterial, antifungal, antiviral and anti-inflammatory effects.

In the course of developing new compounds with tetrazole ring having an anti-cancer activity, the present inventors have synthesized novel tetrazolo hydrazone derivative compounds, confirmed that the compounds have an excellent anti-cancer effect, and then completed the present invention.

DISCLOSURE

Technical Problem

The purpose of the present invention is to provide novel compounds having tetrazole ring, tetrazolo hydrazone derivatives, and use thereof for treating or preventing cancer.

Technical Solution

In one aspect, there is provided tetrazolo hydrazone derivatives represented by the following Formula 1 or pharmaceutically acceptable salts thereof:

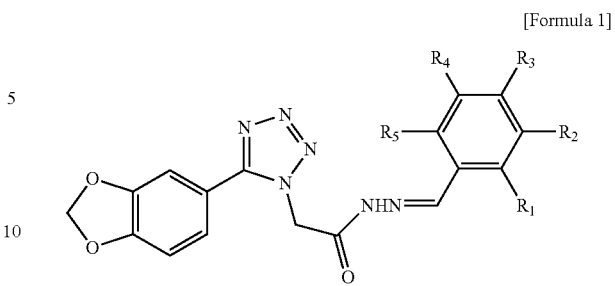

[Formula 1]

wherein, $R_1$, $R_2$, $R_3$, $R_4$ and $R_5$ are independently H, halogen, $NO_2$, $C_{1-4}$ alkyl, $C_{1-4}$ haloalkyl or $C_{1-4}$ alkoxy.

In another aspect, there is provided a pharmaceutical composition for preventing or treating cancer comprising tetrazolo hydrazone derivatives or pharmaceutically acceptable salts thereof.

Advantageous Effects

The novel tetrazolo hydrazone derivatives compounds according to the present invention may inhibit the proliferation of cancer cells in a low molar concentration and inhibit the activity of cancer cells through the regulation of expression of apoptosis-related genes or the like, thus expressing excellent anti-cancer activity, and therefore, can be used effectively in preventing or treating cancer.

MODE FOR CARRYING OUT THE INVENTION

Figure 1:
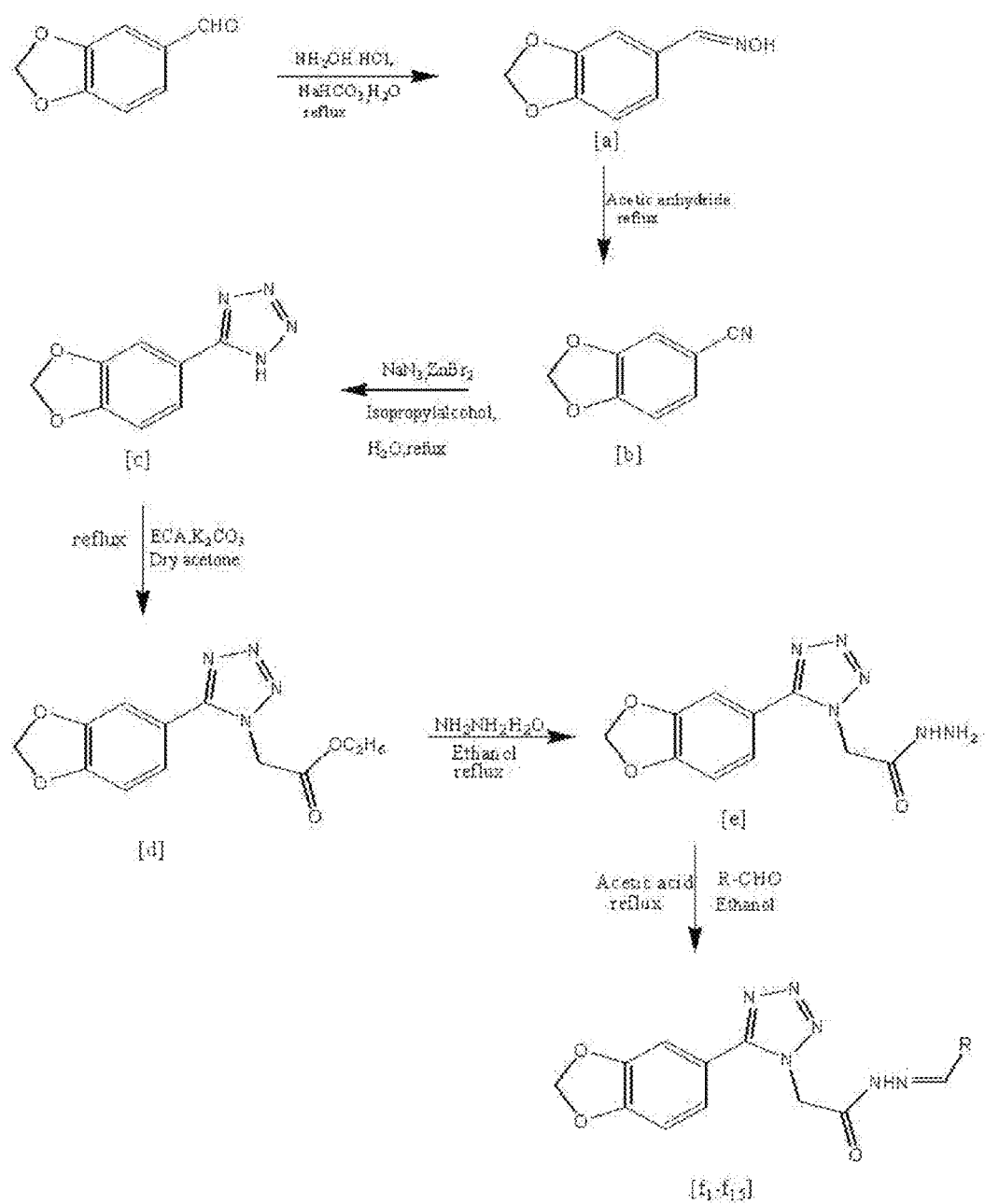
FIG. 1 is a synthesis reaction diagram of tetrazolo hydrazone derivatives of the present invention.

The present invention provides tetrazolo hydrazone derivatives represented by the following Formula 1 or pharmaceutically acceptable salts thereof:

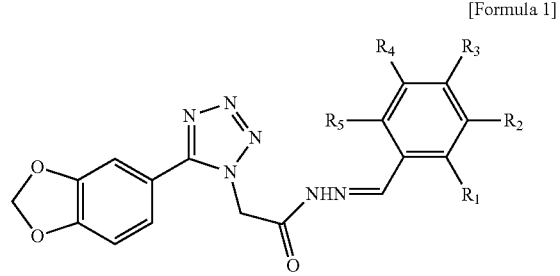

[Formula 1]

wherein, $R_1$, $R_2$, $R_3$, $R_4$ and $R_5$ may be independently H, halogen, $NO_2$, $C_{1-4}$ alkyl, $C_{1-4}$ haloalkyl or $C_{1-4}$ alkoxy.

In one embodiment of the present invention, $R_1$ may be Cl, Br, or I and $R_2$, $R_3$, $R_4$ and $R_5$ may be halogen.

In another embodiment of the present invention, $R_1$, $R_2$, $R_3$, $R_4$ and $R_5$ may be independently halogen or $NO_2$. In one example of the present invention, any one selected from the group of R1, R2, R3, R4 and $R_5$ may be $NO_2$, not selected substituents may be halogen.

In another embodiment of the present invention, $R_1$, $R_2$, $R_3$, $R_4$ and $R_5$ may be independently H or methoxy. In one example of the present invention, R2 and R3, or R3 and R4 may be methoxy, remaining substituents may be H.

In another embodiment of the present invention, the tetrazolo hydrazone derivative may be, but not limited to, 2-[5-(1, 3-Benzodioxol-5-yl)-1H-tetrazol-1-yl]N'-[(2-chlorophenyl)methylidene]acetohydrazide, 2-[5-(1,3-Benzodioxol-5-yl)-1H-tetrazol-1-yl]-N'-[(3,4-dimethoxyphenyl)methylidene]acetohydrazide, 2-[5-(1,3-Benzodioxol-5-yl)-1H-tetrazol-1-yl]N'-[(2-nitrophenyl)methylidene]acetohydrazide, 2-[5-(1, 3-Benzodioxol-5-yl)-1H-tetrazol-1-yl]N'-[(3-nitrophenyl)methylidene]acetohydrazide or 2-[5-(1,3-Benzodioxol-5-yl)-1H-tetrazol-1-yl]N'-[(E)-(4-nitrophenyl)methylidene]acetohydrazide.

The tetrazolo hydrazone derivatives represented by Formula 1 according to the present invention may be used in a form of pharmaceutically acceptable salt in which salt is preferably acid addition salt formed by means of pharmaceutically acceptable free acid. As a free acid can be used inorganic acid and organic acid. Inorganic acid may be hydrochloric acid, bromic acid, sulfuric acid, sulfurous acid or phosphoric acid, and organic acid may be citric acid, acetic acid, maleic acid, fumaric acid, glucoic acid, methane sulfonic acid, acetic acid, gluconic acid, succinic acid, tartaric acid, 4-toluene sulfonic acid, galacturonic acid, embonate, glutamic acid, citric acid or aspartic acid. Preferably, the inorganic acid may be hydrochloric acid, and the organic acid may be methane sulfonic acid. In addition, the tetrazolo hydrazone derivatives of Formula 1 according to the present invention include all salts and hydrates and solvates thereof which can be prepared using a conventional method as well as pharmaceutically acceptable salts.

The addition salts according to the present invention may be prepared using conventional methods. For example, they may be prepared by dissolving the compound of Formula 1 in a water-miscible organic solvent, such as acetone, methanol, ethanol or acetonitrile and adding an excess of organic acids or an excess of aqueous inorganic acid solutions so as to precipitate or crystallize. These addition salts may be obtained by distilling the solvent or excess of acids from the solution or by suctioning and filtering the precipitates.

The tetrazolo hydrazone derivatives of Formula 1 according to the present invention were synthesized from 1,3-benzodioxazole-5-carbaldehyde using multistep reaction system. Specific synthesized examples were shown in Examples and FIG. 1. More specifically, the aldehyde was converted into an oxime which when treated with excess of acetic anhydride yielded piperonylonitrile. The nitrile functionality was converted to corresponding tetrazoles with addition of azide and in situ cyclization using zinc bromide. This tetrazole core molecule was used to synthesize a series of substituted derivatives. All the synthesized compounds were characterized by various spectroscopic techniques, for example, infrared spectroscopy, nuclear magnetic resonance spectrum, mass spectrometry, liquid chromatography, X-ray crystallography, and polarimeter. The molecular structure can be identified by comparison of the elemental analysis calculated values of representative compounds and actual measurement value of the synthesized compounds.

In addition, as confirmed in the following examples, the tetrazolo hydrazone derivatives of Formula 1 according to the present invention inhibit the proliferation of breast cancer cell lines, MCF-7, MDA-Mb-231 and Zr-75 in a low molar concentration and inhibit the activity of cancer cells through the regulation of expression of apoptosis-related genes or the like, thus expressing excellent anti-cancer activity, and therefore, can be used effectively in preventing or treating cancer.

Therefore, the present invention provides a pharmaceutical composition for preventing or treating cancer, comprising the tetrazolo hydrazone derivatives or pharmaceutically acceptable salts thereof. In other words, the present invention provides the use of tetrazolo hydrazone derivatives or pharmaceutically acceptable salts thereof according to the present invention for manufacturing a pharmaceutical composition for preventing or treating cancer. In addition, the present invention provides a method for the preventing or treating cancer, which comprises administering to the subject an effective amount of tetrazolo hydrazone derivatives or pharmaceutically acceptable salts thereof.

In one embodiment of the present invention, the pharmaceutical composition for preventing or treating cancer may comprise the tetrazolo hydrazone derivatives or pharmaceutically acceptable salts thereof in an amount of 0.01-90 wt %, 0.1-90 wt %, 1-90 wt %, or 10-90 wt % based on the total weight of the pharmaceutical composition, but it is not limited to them and can be varied depending on the condition and body weight of a patient and severity of disease.

In another embodiment of the present invention, the pharmaceutical composition for preventing or treating cancer comprising the hydrazone-tetrazole derivatives or pharmaceutically acceptable salts thereof may further comprise one or more selected from the group consisting of carrier, excipient, disintegrants, sweetener, coating agent, expansion agent, lubricants, glydents, flavor, antioxidant, buffer solution, fungistats, diluent, dispersing agent, surfactant, and binders.

Specifically, the carrier, excipient and diluent may be lactose, dextrose, sucrose, sorbitol, mannitol, xylitol, Erythritol, maltitol, starch, acacia gum, alginate, alginate, calcium, Calcium Phosphate, Calcium Silicate, cellulose, methyl cellulose, microcrystalline cellulose, polyvinylpyrrolidone, water, methyl hydroxybenzoate, Propylhydroxybenzoate, talc, magnesium stearate and mineral oil. Solid formulations for oral administration include tablets, pills, powders, granules, capsules, and the like. The solid preparations may be prepared by mixing the composition with one or more of excipients, for example starch, calcium carbonate, sucrose or lactose, gelatin, and the like. Also, in addition to the simple excipients, lubricants such as magnesium stearate or talc may be used. Liquid formulations for oral administration include suspension, internal solution, emulsion, syrup, and the like. In addition to simple diluents such as water and liquid paraffin, various excipients, e.g. wetting agent, sweetener, aromatic, preservative, and the like may be included. Formulations for parenteral administration include sterilized aqueous solution, non-aqueous solution, suspension, emulsion, lyophilized preparation, suppository, and the like. As the non-aqueous solution or suspension, propylene glycol, polyethylene glycol, vegetable oil such as olive oil, injectable ester such as ethyl oleate, and the like may be used. As a base of the suppository, witepsol, macrogol, Tween 61, cocoa butter, laurin butter, glycerogelatin, and the like may be used.

In another embodiment of the present invention, the formulations of the pharmaceutical composition for preventing or treating cancer comprising the tetrazolo hydrazone derivatives or pharmaceutically acceptable salts thereof may be selected from the group consisting of granules, powders, coated tablets, tablets, pills, capsules, suppository, gel, syrup, juice, suspension, emulsion, dropping agent or liquid.

In one embodiment of the present invention, the pharmaceutical composition may be administered using conventional methods, for example, intravenous, intraarterial, intraperitoneal, intramuscular, intrabreastbone, percutaneous, intranasal, local, rectal, oral, intraocular or intradermal pathway.

The effective dosage of the pharmaceutical composition for treating or preventing cancer comprising the tetrazolo hydrazone derivatives or pharmaceutically acceptable salts thereof may vary depending on conditions and body weight of a patient, type and severity of disease, formulation type, route and period of administration, and the like. The effective dosage may be properly selected by those skilled in the art.

In one embodiment of the present invention, the compounds may be administered at a dosage of 0.01-1,000 mg/kg, specifically 0.1-1,000 mg/kg more specifically 0.1-100 mg/kg per day. but it is not limited to them. The administration may be done once or several times a day. However, the aforesaid dosage does not limit the scope of the present disclosure by any means.

In the present invention, the 'subject' may be, but not limited to, mammal including human being.

In one embodiment of the present invention, the cancer may be solid cancer. Preferably, the tetrazolo hydrazone derivatives of Formula 1 of the present invention may be used for treatment of Brain tumor, Low-grade astrocytoma, High-grade astrocytoma, Pituitary adenoma, Meningioma, CNS lymphoma, Oligodendroglioma, Craniopharyngioma, Ependymoma, Brain stem tumor, Head & Neck tumor, Larygeal cancer, Oropgaryngeal cancer, Nasal cavity/PNS tumor, Nasopharyngeal tumor, Salivary gland tumor, Hypopharyngeal cancer, Thyroid cancer, Oral cavity tumor, Chest Tumor, Small cell lung cancer, Non small cell lung cancer, Thymoma, Mediastinal tumor, Esophageal cancer, Breast cancer, Male breast cancer, Abdomen-pelvis tumor, Stomach cancer, Hepatoma, Gall bladder cancer, Billiary tract tumor, pancreatic cancer, Small intestinal tumor, Large intestinal tumor, Anal cancer, Bladder cancer, Renal cell carcinoma, Male genital cancer, Penile cancer, Prostatic cancer, Female genital cancer, Cervix cancer, Endometrial cancer, Ovarian cancer, Uterine sarcoma, Vaginal cancer, Vulva cancer, Urethral cancer or Skin cancer. More preferably, the tetrazolo hydrazone derivatives of Formula 1 of the present invention may be used for treatment of Breast cancer.

Hereinafter, embodiments of the present invention will be described in detail. The present invention is not restricted to the following embodiments, and many variations are possible within the spirit and scope of the present invention. The embodiments of the present invention are provided in order to more completely explain the present invention to anyone skilled in the art.)

Preparation Example 1

Preparation of Tetrazolo Hydrazone Derivatives and Analysis of Structure

1. Materials and Analysis Methods

Solvents and organic reagents purchased from Sigma Aldrich, Merck (Germany) was used without purification. Melting points (mp) were performed using a Mel-temp instrument, and the results are uncorrected. Precoated aluminum sheets (silica gel 60 $F_{254}$, Merck Germany) were used for thin-layer chromatography (TLC), spots were visualized under UV light. Elemental analysis was performed on Heraeus Vario EL III analyzer of Central Drug Research Institute Lucknow, Uttar Pradesh, India and the results were within ±0.3% of theoretical values. Electronic spectra were recorded on Shimadzu UV 1601 PC UV-Visible spectrophotometer. IR spectra were recorded on a PerkineElmer model 1600 FT-IR RX1 spectrophotometer as KBr discs. $^1$H NMR and $^{13}$C NMR spectra were recorded on Bruker Avance 300 spectrometer using DMSO-$d_6$ as solvent with TMS as internal standard. Splitting patterns are designated as follows; s, singlet; d, doublet; t, triplet; and m, multiplet. Chemical shift values are given in ppm. ESI-MS was recorded on a Micromass Quattro II triple quadrupole mass spectrometer.

2. Preparation Methods 5-(1,3-benzodioxol-5-yl)-1-tetrazole molecular was synthesized from 1,3-benzodioxazole-5-carbaldehyde using multistep reaction system. The aldehyde was converted into an oxime which when treated with excess of acetic anhydride yielded piperonylonitrile. The nitrile functionality was converted to corresponding tetrazoles with addition of azide and in situ cyclization using zinc bromide. This tetrazole core molecule was used to synthesize a series of substituted derivatives. The synthesize pathway was described in FIG. 1. All the compounds were characterized by various spectroscopic techniques. Hereafter, the synthesis methods of each step are illustrated in detail.

1) General Procedure for the Synthesis of Piperonal Oxime [a]

To a solution of aldehyde (1 eq) and hydroxylamine hydrochloride (1.25 eq) in water (5 mL), a solution of sodium bicarbonate (1.25 eq) in water (10 mL) was added gradually with stirring. The mixture was stirred for further 2-5 h with the formation of a solid precipitate. The compound was filtered and air dried.

2) General Procedure for the Synthesis of Piperonal Nitrile [b]

To a 250 ml round-bottomed flask, a mixture of piperonal oxime and acetic anhydride (20 mL) was added and refluxed with stirring for 24 h. The reaction mixture was poured into ice cold water to obtain a solid precipitate. The precipitate was filtered, and air dried.

3) General Procedure for the Preparation of 5-(1,3-benzodioxol-5-yl)-1H-tetrazole [c]

To a 250 ml round-bottomed flask, a mixture of nitrile (20 mmol), sodium azide (22 mmol), zinc bromide (20 mmol), 40 mL of water and isopropylalcohol (10 mL) were added. The reaction mixture was refluxed for 24 h with stirring. HCl (3 N, 30 mL) and ethyl acetate (100 mL) were added and reaction was continued until the solid material present in the flask disappeared and pH of aqueous layer reached to 1. If necessary, additional ethyl acetate was added. The organic layer was isolated and aqueous layer was treated with 2×100 mL of ethyl acetate. The combined organic layers were evaporated. 200 mL of 0.25 N NaOH was added, and the mixture was stirred for 30 min, until the original precipitate was dissolved and a suspension of zinc hydroxide was formed. The suspension was filtered, and the solid washed with 20 mL of 1 N NaOH. To the filtrate was added 40 mL of 3 N HCl with vigorous stirring causing the tetrazole to precipitate. The tetrazole was filtered and washed with 2×20 mL of 3 N HCl and dried in a drying oven to furnish the tetrazole as a white or yellow powder. If necessary, the solid was triturated with hexane or 10% ethyl acetate in hexane.

6.156 (s, $2H_2O$—$CH_2$—O), 7.135 (J=8.1, d, 1H, Ar—H), 7.548 (s, 1H, Ar—H), 7.596 (J=7.8, d, 1H, Ar—H), 11.011 (s, 1H, NH).

4) General Procedure for the Preparation of Ethyl[5-(1,3-benzodioxol-5-yl)-1H-tetrazol-1-yl]acetate [d]

A mixture of 5-(1,3-benzodioxol-5-yl)-1H-tetrazole (10 mmol), ethyl chloroacetate (10 mmol) and potassium carbonate (15 mmol) in dry acetone (100 mL) was refluxed for 24 h. The reaction mixture was filtered, the solvent was distilled. The crude ester thus obtained was purified by recrystallization from ethanol.

1.117-1.263 (t, 3H, $CH_3$), 4.101-4.265 (m, 2H, $CH_2$), 5.851 (s, 2H, $CH_2$), 6.141 (s, $2H_2O$—$CH_2$—O), 7.094 (J=8.1, d, 1H, Ar—H), 7.523 (s, 1H, Ar—H), 7.619 (J=9.6, d, 1H, Ar—H).

5) General Procedure for the Preparation of 2-[5-(1,3-benzodioxol-5-yl)-1H-tetrazol-1-yl]acetohydrazide [e]

A mixture of ethyl[5-(1,3-benzodioxol-5-yl)-1H-tetrazol-1-yl]acetate (10 mmol) and hydrazone hydrate (99%, 10 mmol) in ethanol (50 mL) was refluxed for 8 h. The solution on cooling gave a solid mass of hydrazide, which was collected by filtration, and recrystallized from ethanol.

5.377 (s, 2H, $CH_2$), 6.099 (s, $2H_2O$—$CH_2$—O), 7.051 (J=8.1, d, 1H, Ar—H), 7.468 (s, 1H, Ar—H), 7.564 (J=8.1, d, 1H, Ar—H), 9.598 (s, 2H, $NH_2$).

6) General Procedure for the Preparation of Compounds $f_1$-$f_{15}$

A mixture of compound e (10 mmol), appropriate aldehyde and few drops of glacial acetic acid in ethanol (50 mL) was refluxed for 12 h. The product was precipitated, collected by filtration and recrystallized from ethanol. Then, anti-cancer effects of the compound $f_1$-$f_{15}$ were analyzed.

f1: 2-[5-(1,3-benzodioxol-5-yl)-1H-tetrazol-1-yl]-N'-[4-chlorophenyl-methylidene]acetohydrazide Yield: 92%; mp 206-208° C.; white crystals; $C_{17}H_{13}N_6O_3Cl$: C58.28, H4.03, N23.99. found C, 58.29, H, 4.02, N, 23.98; $IRv_{max}(cm^{-1})$: 1031 (C—N), 1617 (C=N), 1693 (C=O), 3001 (CH—Ar), 3210 (NH); $^1$H NMR DMSO-d6/δ (ppm): 5.656 (s, 2H, $CH_2$), 6.105 (s, 2H, O—$CH_2$—O), 7.083 (J=8.1, d, 1H, Ar—H), 7.521 (s, 1H, Ar—H), 7.619 (J=8.1, d, 1H, Ar—H), 7.739 (J=11.4, d, 1H, Ar—H), 8.059 (s, 1H, HC=N), 12.038 (s, 1H, NH); $^{13}$C NMR DMSO-d6/δ (ppm): 55.44[$CH_2$], 101.71[O—C—O], 106.20, 109.07, 114.44, 120.55, 120.88, 124.99, 130.54, 148.03, 149.21, 163.99, 165.45, 168.11[CH=N], 170.63[C=O]; ESI-MS (m/z): [M$^+$+1] 384.07 (384.78).

f2: 2-[5-(1,3-benzodioxol-5-yl)-1H-tetrazol-1-yl]-N'-[(2-chlorophenyl)methylidene]acetohydrazide Yield 93%; mp 198-200° C.; white crystals; $C_{17}H_{13}N_6O_3Cl$: C58.28, H4.03, N, 23.99. found C58.29, H4.02, 23.98; $IRv_{max}(cm^{-1})$: 1039 (C—N), 1605 (C=N), 1702 (C=O), 2955 (CH—Ar), 3128 (NH); $^1$H NMR DMSO-d6/δ (ppm): 5.638 (s, 2H, $CH_2$), 6.109 (s, 2H, O—$CH_2$—O), 7.06 (J=7.8, d, 1H, Ar—H), 7.593 (J=8.1, d, 1H, Ar—H), 8.056 (J=7.5, d, 1H, Ar—H), 7.392-7.527 (m, 2H, Ar—H), 8.424 (s, 1H, HC=N), 12.118 (s, 1H, NH); $^{13}$C NMR DMSO-d6/δ (ppm): 55.41[$CH_2$], 101.69[O—C—O], 106.19, 109.10, 114.50, 120.35, 120.43, 124.79, 130.44, 148.23[CH=N], 149.23, 163.79, 165.55, 168.13, 170.65 [C=O]; ESI-MS (m/z): [M$^+$+1] 384.07 (384.78).

f3: 2-[5-(1,3-benzodioxol-5-yl)-1H-tetrazol-1-yl]-N'-[(4-ethoxyphenyl)methylidene]acetohydrazide Yield 93%; mp 208-210° C.; white crystals; $C_{19}H_{18}N_6O_4$: C57.86, H4.60, N, 21.31. found: C57.87, H4.59, N21.30; $IRv_{max}(cm^{-1})$: 1043 (C—N), 1607 (C=N), 1688 (C=O), 2959 (CH—Ar), 3142 (NH); $^1$H NMR DMSO-d6/δ (ppm): 1.285-1.331 (t, 3H, $CH_3$), 4.009-4.078 (dd, 2H, $CH_2$), 5.587 (s, 2H, $CH_2$), 6.034 (s, 2H, O—$CH_2$—O), 6.942 (J=8.4, d, 1H, Ar—H), 7.061 (J=8.1, d, 1H, Ar—H), 7.495 (s, 1H, Ar—H), 7.591-7.688 (m, 2H, Ar—H), 8.162 (s, 1H, HC=N), 11.811 (s, 1H, NH); $^{13}$C NMR DMSO-d6/δ (ppm): 25.74 [$CH_3$], 55.41[$CH_2$], 65.22[O—$CH_2$], 101.69[O—C—O], 106.19, 109.10, 114.50, 120.35, 120.43, 124.79, 130.44, 148.23[CH=N], 149.23, 163.79, 165.55, 168.13, 170.65 [C=O], ESI-MS (m/z): [M$^+$+1] 394.14 (394.38).

f4: 2-[5-(1,3-benzodioxol-5-yl)-1H-tetrazol-1-yl]-N'-[(4-methoxyphenyl)methylidene]acetohydrazide Yield 95%; mp 198-200° C.; white crystals; $C_{18}H_{16}N_6O_4$: C56.84, H4.24, N, 22.10. found: C56.85, H4.25, N22.11%; $IRv_{max}(cm^{-1})$: 1043 (C—N), 1606 (C=N), 1685 (C=O), 3000 (CH—Ar), 3210 (NH); $^1$H NMR DMSO-d6/δ (ppm): 3.331 (s, 3H, $OCH_3$), 5.614 (s, 2H, $CH_2$), 6.134 (s, 2H, O—$CH_2$—O), 6.977 (J=13.5, d, 1H, Ar—H), 7.092 (J=7.8, d, 1H, Ar—H), 7.526 (s, 1H, Ar—H), 7.623-7.714 (m, 2H, Ar—H), 8.015 (s, 1H, HC=N), 11.831 (s, 1H, NH); $^{13}$C NMR DMSO-d6/δ (ppm): 55.48 [$OCH_3$], 57.06 [$CH_2$], 101.70[O—C—O], 106.19, 109.06, 114.48, 120.58, 120.87, 124.96, 130.54, 148.03[CH=N], 149.21, 163.98, 165.44, 168.16, 170.61[C=O]; ESI-MS (m/z): [M$^+$+1] 380.12 (380.12)

f5: 2-[5-(1,3-benzodioxol-5-yl)-1H-tetrazol-1yl]-N'-[phenylmethylidene]acetohydrazide Yield 93%; mp 204-206° C.; white crystals; $C_{17}H_{14}N_6O_3$: C58.28, H4.03, N23.99. found C58.29, H4.02, N24.01; $IRv_{max}$ (cm$^{-1}$): 1037 (C—N), 1607 (C=N) 1687 (C=O), 2909 (CH—Ar), 3068 (NH); $^1$H NMR DMSO-d6/δ (ppm): 5.627 (s, 2H, $CH_2$), 6.082 (s, 2H, O—$CH_2$—O), 7.076 (J=8.1, d, 1H, Ar—H), 7.431 (J=3.6, d, 1H, Ar—H), 7.510 (s, 1H, Ar—H), 7.606 (J=8.1, d, 1H, Ar—H), 7.735-7.758 (m, 1H, Ar—H), 8.056 (s, 1H, HC=N), 11.954 (s, 1H, NH); $^{13}$C NMR DMSO-d6/δ (ppm): 56.00[$CH_2$], 101.69[O—C—O], 106.21, 109.06, 120.67, 120.85, 127.12, 127.27, 128.77, 130.19, 133.73, 144.94[CH=N], 148.03, 149.17, 162.20, 163.95[C=O]; ESI-MS (m/z): [M$^+$+1] 350.11 (350.11)

f6: 2-[5-(1,3-benzodioxol-5-yl)-1H-tetrazol-1-yl]-N'-[(4-methylphenyl)methylidene]acetohydrazide Yield 95%; mp 203-205° C.; white crystals; $C_{18}H_{16}N_6O_3$: C58.28, H4.03, N23.99. found C58.27, H4.02, N24.00; $IRv_{max}(cm^{-1})$: 1034 (C—N), 1607 (C=N), 1676 (C=O), 2911 (CH—Ar), 3199 (NH); $^1$H NMR DMSO-d6/δ (ppm): 2.317 (s, 3H, $CH_3$), 5.609 (s, 2H, $CH_2$), 6.016 (s, 2H, O—$CH_2$—O), 7.062 (J=8.7, d, 1H, Ar—H), 7.227 (J=7.8, d, 1H, Ar—H), 7.498 (s, 1H, Ar—H), 7.583-7.681 (m, 2H, Ar—H), 8.012 (s, 1H, HC=N), 11.861 (s, 1H, NH); $^{13}$C NMR DMSO-d6/δ (ppm): 25.69[CH$_3$], 56.10[CH$_3$], 101.68 [O—C—O], 106.22, 109.16, 120.77, 120.87, 127.22, 127.24, 128.75, 130.18, 133.59, 144.82[CH=N], 148.13, 149.27, 162.21[C=O], 163.91; ESI-MS (m/z): [M$^+$+1] 364.16 (364.13).

f7: 2-[5-(1,3-benzodioxol-5-yl)-1H-tetrazol-1-yl]-N'-[(2-ethoxyphenyl)methylidene]acetohydrazide Yield 96%; mp 196-198° C.; white crystals; C$_{19}$H$_{18}$N$_6$O$_4$: C57.86, H4.60, N, 21.31. found C57.87, H4.59, N21.30; IRv$_{max}$(cm$^{-1}$): 1035 (C—N), 1608 (C=N), 1685 (C=O), 2905 (CH—Ar), 3211 (NH); $^1$H NMR DMSO-d6/δ (ppm): 1.349-1.414 (t, 3H, CH$_3$), 4.089-4.156 (m, 2H, CH$_2$), 5.612 (s, 2H, CH$_2$), 6.074 (s, 2H, O—CH$_2$—O), 6.968-7.429 (m, 2H, Ar—H), 7.525 (s, 1H, Ar—H), 7.617 (J=2.1, d, 1H, Ar—H), 7.644 (J=1.8, d, 1H, Ar—H), 7.898 (J=7.8, d, 1H, Ar—H), 8.440 (s, 1H, HC=N), 11.898 (s, 1H, NH); $^{13}$C NMR DMSO-d6/δ (ppm): 15.74[CH$_3$], 55.41[CH$_2$], 63.91 [O—CH$_2$], 101.69[O—C—O], 106.19, 109.10, 114.50, 120.35, 120.43, 124.79, 130.44, 148.23[CH=N], 149.23, 163.79, 165.55, 168.13, 170.65[C=O]; ESI-MS (m/z): [M$^+$+1] 394.13 (394.14).

f8: 2-[5-(1,3-benzodioxol-5-yl)-1H-tetrazol-1-yl]-N'-[(3,4-dimethoxyphenyl)methylidene]acetohydrazide Yield 94%; mp 200-202° C.; white crystals; C$_{19}$H$_{18}$N$_6$O$_5$: C55.61, H4.42, N20.48. found C55.60, H4.41, N20.49; IRv$_{max}$(cm$^{-1}$): 1033 (C—N), 1604 (C=N), 1685 (C=O), 2960 (CH—Ar), 3222 (NH); $^1$H NMR DMSO-d6/δ (ppm): 3.790 (s, 3H, OCH$_3$), 3.806 (s, 3H, OCH$_3$), 5.591 (s, 2H, CH$_2$), 6.065 (s, 2H, O—CH$_2$—O), 6.974 (J=8.1, d, 1H, ArH), 7.184 (J=8.4, d, 1H, Ar—H), 7.298 (s, 1H, Ar—H), 7.377 (s, 1H, Ar—H), 7.502 (s, 1H, Ar—H), 7.603 (J=8.1, d, 1H, Ar—H), 7.970 (s, 1H, HC=N), 11.804 (s, 1H, NH); $^{13}$C NMR DMSO-d6/δ (ppm): 55.48[CH$_2$], 57.06[OCH$_3$], 101.70[O—C—O], 106.19, 109.06, 114.48, 120.58, 120.87, 124.96, 130.54, 148.03[CH=N], 149.21, 163.98, 165.44, 168.16, 170.61[C=O]; ESI-MS (m/z): [M$^+$+1] 410.13 (410.13).

f9: 2-[5-(1,3-benzodioxol-5-yl)-1H-tetrazol-1-yl]-N'-[thiophen-2-I methylidene]acetohydrazide Yield 95%; mp 200-202° C.; white crystals; C$_{15}$H$_{12}$N$_6$O$_3$S: C50.56, H3.39, N23.58. found C50.57, H3.40, N23.57; IRv$_{max}$(cm$^{-1}$): 1038 (C—N), 1501 (C=N), 1692 (C=O), 2971 (CH—Ar), 3139 (NH); $^1$H NMR DMSO-d6/δ (ppm): 5.615 (s, 2H, CH$_2$), 5.973 (s, 2H, O—CH$_2$—O), 7.089-7.503 (m, 3H, Ar—H), 7.523 (s, 1H, Ar—H), 7.643 (J=1.2, d, 1H, Ar—H), 7.675 (J=4.8, d, 1H, Ar—H), 8.255 (s, 1H, HC=N), 11.926 (s, 1H, NH); $^{13}$C NMR DMSO-d6/δ (ppm): 53.6 [CH2]; 101.20 [O—C—O], 112.3, 115.8, 120.8, 124.0, 125.1, 125.8, 127.1, 127.4, 144.2, 148.8, [CH=N], 149.3, 163.5, 173.2 [C=O]; ESI-MS (m/z): [M$^+$+1] 356.06 (356.07).

f10: 2-[5-(1,3-benzodioxol-5-yl)-1H-tetrazol-1yl]-N'-[(2-nitrophenyl)methylidene]acetohydrazide Yield 97%; mp 210-212° C.; yellow crystals; C$_{17}$H$_{13}$N$_7$O$_5$: C51.65, H3.31, N24.80. found C51.66, H3.30, N24.81; IRv$_{max}$(cm$^{-1}$): 1039 (C—N), 1614 (C=N), 1693 (C=O), 2967 (CH—Ar), 3148 (NH); $^1$H NMR DMSO-d6/δ (ppm): 5.685 (s, 2H, CH$_2$), 6.138 (s, 2H, O—CH$_2$—O), 7.069 (J=16.2, d, 1H, Ar—H), 7.529 (s, 1H, Ar—H), 7.625-8.127 (m, 4H, Ar—H), 8.200 (J=7.8, d, 1H, Ar—H), 8.473 (s, 1H, HC=N), 12.257 (s, 1H, NH); $^{13}$C NMR DMSO-d6/δ (ppm): 53.80[CH$_2$], 101.71[O—C—O], 106.24, 109.09, 120.64, 123.94, 128.14, 140.03, 142.65[CH=N], 147.96, 148.25, 149.21, 166.72[C=O], ESI-MS (m/z): [M$^+$+1] 395.09 (395.1).

f11: 2-[5-(1,3-benzodioxol-5-yl)-1H-tetrazol-1-yl]-N'-[(4-ethylphenyl)methylidene]acetohydrazide Yield 93%; mp: 200-202° C.; white crystals; C$_{19}$H$_{18}$N$_6$O$_3$: C60.31, H4.79, N22.21. found C60.30, H4.80, 22.22; IRv$_{max}$ (cm$^{-1}$): 1034 (C—N), 1528 (C=N), 1680 (C=O), 2959 (CH—Ar), 3198 (NH); $^1$H NMR DMSO-d6/δ (ppm): 1.169-1.216 (t, 3H, CH$_3$), 2.504-2.655 (tetra, 2H, CH$_2$), 5.629 (s, 2H, CH$_2$), 6.076 (s, 2H, O—CH$_2$—O), 7.089 (J=7.8, d, 1H, Ar—H), 7.281 (J=6.9, d, 1H, Ar—H), 7.625-7.675 (m, 2H, Ar—H), 7.525 (s, 1H, Ar—H), 8.042 (s, 1H, HC=N), 11.903 (s, 1H, NH); $^{13}$C NMR DMSO-d6/δ (ppm): 14.81[CH$_3$], 32.80[CH$_2$], 53.66[CH$_2$], 101.11[O—C—O], 115.12, 115.82, 119.98, 124.51, 129.40, 129.61, 130.56, 131.93, 136.42, 142.99[CH=N], 147.73, 149.21, 163.42, 172.31 [C=O]; ESI-MS (m/z): [M$^+$+1] 379.14 (378.14).

f12: 2-[5-(1,3-benzodioxol-5-yl)-1H-tetrazol-1yl]-N'-[(3-nitrophenyl)methylidene]acetohydrazide Yield 93%; mp 208-210° C.; yellow crystals; C$_{17}$H$_{13}$N$_7$O$_5$: C51.65, H3.31, N24.80. found C51.66, H3.30, 24.81; IRv$_{max}$(cm$^{-1}$): 1035 (C—N), 1615 (C=N), 1703 (C=O), 2964 (CH—Ar), 3102 (NH); $^1$H NMR DMSO-d6/δ (ppm): 5.343 (s, 2H, CH$_2$), 5.962 (s, 2H, O—CH$_2$—O), 6.910 (J=7.8, d, 1H, Ar—H), 7.566 (s, 1H, Ar—H), 7.588-7.719 (m, 1H, Ar—H), 8.036 (J=8.1, d, 1H, Ar—H), 8.231 (J=8.1, d, 1H, Ar—H), 8.509 (s, 1H, HC=N), 11.092 (s, 1H, NH); $^{13}$C NMR DMSO-d6/δ (ppm): 53.79 [CH$_2$], 101.80 [O—C—O], 106.26, 109.11, 120.54, 123.84, 128.40, 140.23, 142.39 [CH=N], 147.12, 148.23, 149.31, 166.66[C=O]; ESI-MS (m/z): [M$^+$+1] 395.09 (395.1).

f13: 2-[5-(1,3-benzodioxol-5-yl)-1H-tetrazol-1-yl]-N'-[furan-2-ylmethylidene]acetohydrazide Yield 95%; mp 212-214° C.; white crystals; C$_{15}$H$_{12}$N$_6$O$_4$: C52.94, H3.55, N24.70. found C52.95, H3.56, N24.71; IRv$_{max}$(cm$^{-1}$): 1034 (C—N), 1612 (C=N), 1693 (C=O), 2918 (CH—Ar), 3124 (NH); $^1$H NMR DMSO-d6/δ (ppm): 5.601 (s, 2H, CH$_2$), 5.963 (s, 2H, O—CH$_2$—O), 6.619 (J=1.8, d, 1H, Ar—H), 7.058-7.091 (m, 1H, Ar—H), 7.492 (s, 1H, Ar—H), 7.587 (J=8.1, d, 1H, Ar—H), 8.108 (s, 1H, HC=N), 11.898 (s, 1H, NH); $^{13}$C NMR DMSO-d6/δ (ppm): 53.63 [CH$_2$]; 101.23 [O—C—O], 105.91, 109.91, 112.33, 115.83, 120.82, 124.02, 134.72, 143.99[CH=N], 148.83, 149.11, 149.31, 163.52, 170.11[C=O]; ESI-MS (m/z): [M$^+$+1] 340.09 (340.09).

f14: 2-[5-(1,3-benzodioxol-5-yl)-1H-tetrazol-1-yl]-N'-[(E)-(4-nitrophenyl)methylidene]acetohydrazide Yield 97%; mp 204-206° C.; white crystals; C$_{17}$H$_{13}$N$_7$O$_5$: C51.65, H3.31, N24.80. found C51.66, H3.32, N24.81; IRv$_{max}$(cm$^{-1}$): 1036 (C—N), 1599 (C=N), 1689 (C=O), 2913 (CH—Ar), 3089 (NH); $^1$H NMR DMSO-d6/δ (ppm): 5.672 (s, 2H, CH$_2$), 6.103 (s, 2H, O—CH$_2$—O), 7.066 (J=8.1, d, 1H, Ar—H), 7.498 (s, 1H, Ar—H), 7.420 (J=1.8, d, 1H, Ar—H), 7.997 (J=8.7, d, 1H, Ar—H), 8.244 (J=8.7, d, 1H, Ar—H), 8.148 (s, 1H, HC=N), 11.091 (s, 1H, NH); $^{13}$C NMR DMSO-d6/δ (ppm): 53.09[CH$_2$], 101.67[O—C—O], 106.44, 109.13, 120.59, 123.88, 128.14, 140.13, 142.75 [CH=N], 147.86, 148.31, 149.43, 166.41[C=O]; ESI-MS (m/z): [M$^+$+1] 395.09 (395.1).

Test Example 1

In Vitro Anti-Cancer Activity Analysis in Human Breast Cancer Cell

Anti-cancer activities of the compounds $f_1$-$f_{15}$ on human breast cancer cell line were tested in ER positive (MCF-7) and ER negative (MDA-Mb-231 and Zr-75) cell lines. The human breast cancer cell lines MCF-7 and MDA-MB-231 were cultured in Dulbecco's Modified Eagle's Medium (DMEM) supplemented with 10% fetal bovine serum (FBS) (HyClone Laboratories, Logan, Utah, USA) and 1% penicillin: streptomycin (Invitrogen, Carlsbad, Calif., USA) in 12 well plates. The test compounds $f_1$-$f_{15}$ were dissolved in DMSO and one microliter of the stock solution was used per milliliter of the culture to make a working concentration1 $1\times10^{-5}$, $1\times10^{-6}$ and $1\times10^{-7}$ M. Each test includes control wells. The cell suspension was diluted to $1\times10^4$ cells/mL by adding fresh medium, and 1 mL of this suspension was added to the test and control wells. The plates were incubated at 37° C. under CO$_2$ for 24 h. After incubation, the culture media was changed and cells were treated with 1 mL/mL of stock solution. Cells were incubated at 37° C. under CO$_2$ for 48 h. The growth of the cells was checked with a low power microscope and MTT assay was used to confirm the viability. In the similar experiments, the ZR-75 cells were grown in RPMI 1640 (HyClone Laboratories, Logan, Utah, USA) supplemented with 10% fetal bovine serum (FBS) (HyClone Laboratories, Logan, Utah, USA) and 1% penicillin: streptomycin (Invitrogen, Carlsbad, Calif., USA).

Figure 2:
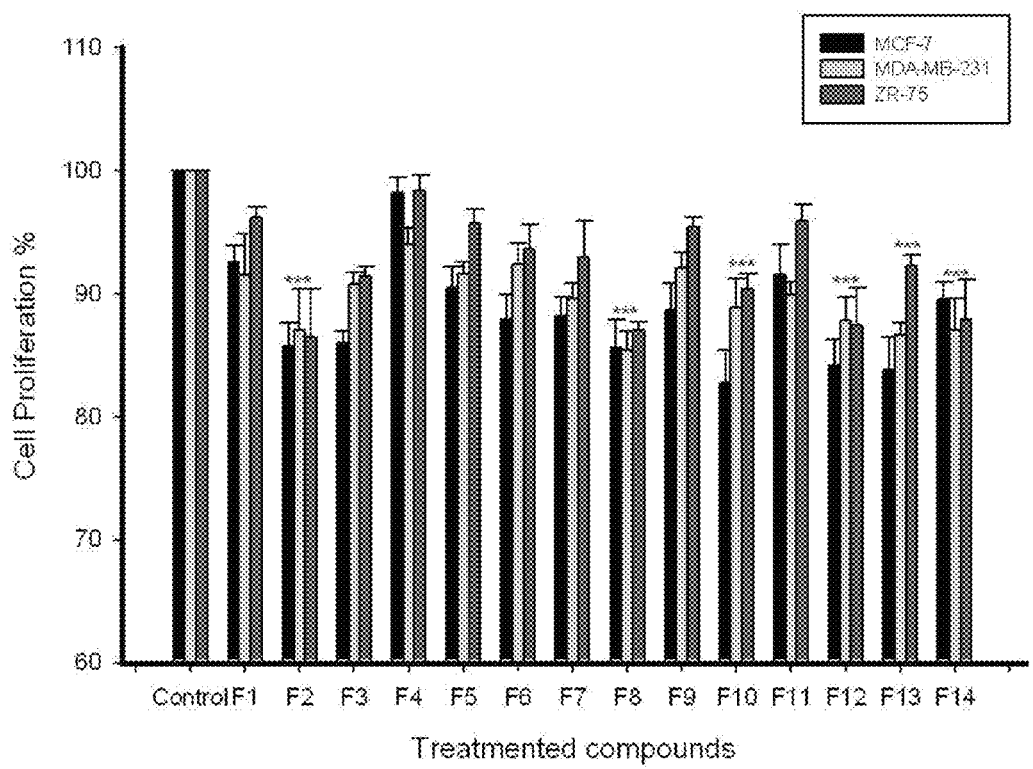
FIG. 2 shows anti-proliferative effects of tetrazolo hydrazone derivatives of the present invention in MCF-7, MDA-Mb-231 and Zr-75 cell lines. Among the total synthesized compounds f1-f15, compounds f2, f8, f10, f12 and f14 of the present invention showed excellent anti-proliferative activity.

The results for each compound on the target MCF-7, MDA-Mb-231 and Zr-75 cell line are shown in FIG. 2. The results for each compound are reported as percent growth (GP %) of treated cells compared to untreated controls. The inhibitory effects were detectable in compounds 2, 8, 10, 12 and 14 among the compounds $f_1$-$f_{15}$. These compounds showed a negative growth of 10-30% compared to the untreated cells. The percent growth inhibition of compounds varied not only with the substituent groups but also with the nature of the cell line.

More specifically, as shown in FIG. 2, the compounds f10, f12 and f14 comprising phenyl group with ortho, meta or para-substituted nitro group were found more anti-proliferative effects on MCF-7 cells growth. Compound f8 comprising 3,4-dimethoxy phenyl substituent showed more anti-proliferative effects in ER negative MDA-MB-231 and ZR-75 cell lines.

Test Example 2

Total RNA Extract and Gene Expression Analysis Using Real Time RT-PCR

To investigate the various effects of various cell lines, the expression levels of different breast cancer marker genes were tested after treating the compounds.

Total RNA was extracted from the cells using Trizol™ reagent, stored in diethylpyrocarbonate-treated water at −80° C. until use. Total 2 μg of RNA was used for cDNA synthesis. All the primer used in examples of the present invention were designed with Primer 3 software (http://frodo.wi.mit.edu) using sequence information listed at NCBI. Following conditions were applied for the RT-PCR: pre-denaturation of the synthesized cDNA at 95° C. for 10 min followed by 40 cycles of denaturation at 95° C. for 33 s, annealing at each gene-specific primer Tm (° C.), and extension at 72° C. for 33 s. 1.2% of the agarose gel electrophoresis were used to verify the purity of the amplified genes.

Figure 3:
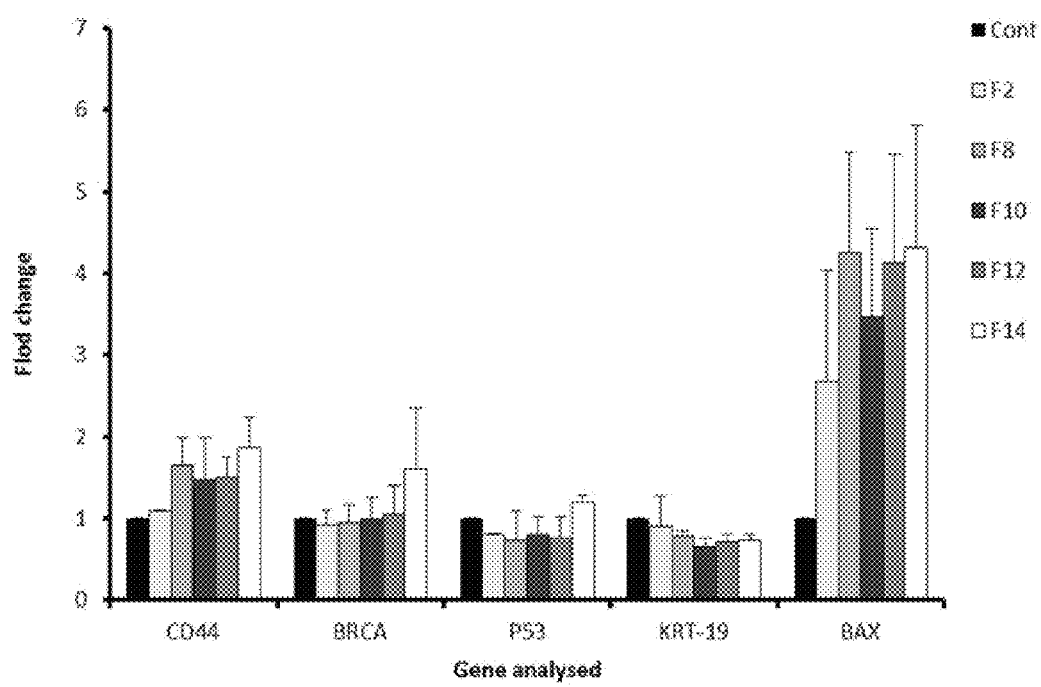
FIG. 3 is a result graph showing the expression level changes of different breast cancer marker genes in the MCF-7 cells following treatment with compounds according to an example of the present invention.
Figure 4:
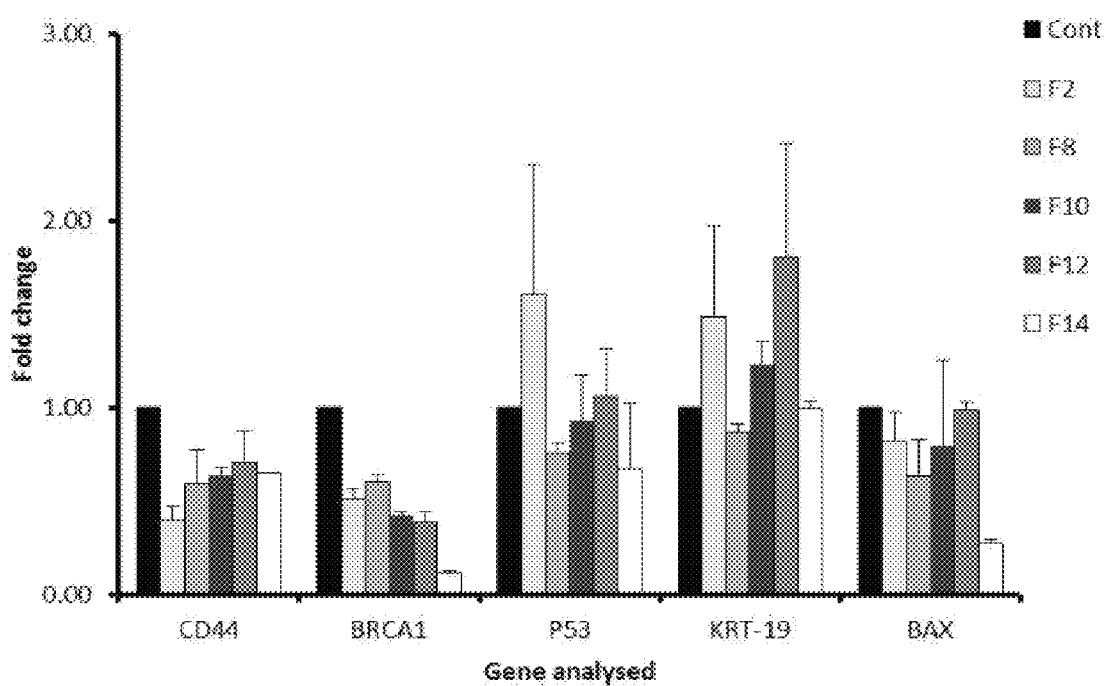
FIG. 4 is a result graph showing the expression level changes of different breast cancer marker genes in MDA-MB-23 cells following treatment with compounds according to an example of the present invention; and, FIG. 5 shows toxicity testing results of tetrazolo hydrazone derivatives of the present invention.

The result in MCF-7 cells was shown in FIG. 3, and the result in MDA-Mb-231 cells as shown in FIG. 4.

Referring to FIG. 3, the expression of BAX in MCF-7 cells was increased more than two fold by treatment of f2, f8, f10, f12 and f14 compounds. A defect in the expression of BAX at mRNA and protein level has been found proportional to apoptosis. Furthermore, restoration of BAX expression in breast cancer cell lines inhibits tumorigenicity and increased sensitivity to drug therapy. This demonstrated that the compounds of the present invention showed a better inhibitory effect at mRNA level. However the expression level was little decreased in MDA-MB-231, an ER negative cell line.

The CD44 gene expression is related to prognosis and metastasis. Increased expression of CD44 has been correlated with poor prognosis in diseases, such as thyroid, prostate and breast cancer. Referring to FIG. 3, the expression of CD44 in MCF-7 cells was increased by treatment of f2, f8, f10, f12 and f14 compounds. Especially, the expression was increased about two fold by treatment of compounds 8 and 10. This result shows that these compounds have ability to decrease the prognosis of the cell. The decrease in expression of CD44 in MDA-MB-231 cells may be due to the highly aggressive and mesenchymal-type behavior.

BRAC-1 is a caretaker gene which produces breast cancer type-1 susceptible protein, responsible for DNA repairing. However the mutations in BRAC-1 gene lead to an increased risk of breast cancer and ovarian cancer. The decrease in expression of BRAC-1 gene is directly proportional to prognosis of the disease. FIG. 4 shows the effect of f2, f8, f10, f12 and f14 compounds on expression of BRAC-1 in MDA-MB-231 cells. From the gene expression, a minimum of two folds decrease was found upon treatment. Especially, the compound 8 having p-nitrophenyl substituent had highly suppressed BRAC-1. In MCF-7 cells also (see FIG. 3), we can find a slight decrease in BRAC-1 expression, however the results are not significant. In similar cases the RNA expression of P53 and KRT-19 was found with low statistical significance.

Test Example 2

MMT Assay

Human liver carcinoma cell line (HepG2) were cultured in DMEM media supplemented with 10% fetal bovine serum (FBS) (HyClone Laboratories, Logan, Utah, USA) and 1% penicillin: streptomycin at 37° C. in a saturated humidity atmosphere containing 95% air/5% CO$_2$. The cells when reached to the 70% confluence were treated with $10^{-5}$ M of the tetrazoles compound f1-f15. The cells were subjected to MTT assay for confirming the viability.

For viability testing, The culture medium was aspirated and cells were washed twice with DMEM to remove the residual activity of FBS. 500 mL of 10% MTT (5 mg, thiazolyl blue tetrazolium bromide, M2128 from Sigma in 1 mL of PBS) in DMEM were added to each well of cells and incubated for 3 h at 37° C. under CO$_2$ atmosphere. The MTT solution was aspirated and 500 mL of DMSO were added to dissolve the purple color. The plates were placed on rotator for 10 min and 100 mL of blue colored solution was transferred to the 96 well plate. Optical density was measured at 510 nm using a Versa Max microplate reader (Sunnyvale, Calif., USA)

Figure 5:
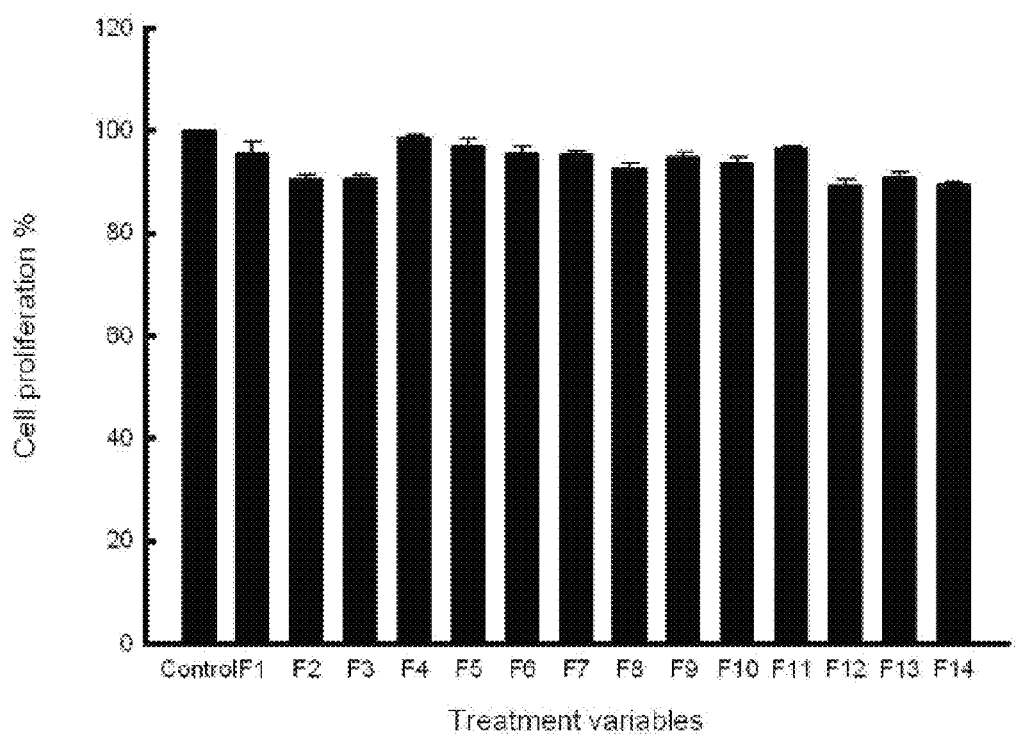

As shown in FIG. 5, the toxicity of all compounds (compound f1-f15) was not detected comparing to control group in Human liver carcinoma cell line (HepG2).

Hereinafter, the formulation examples of the pharmaceutical composition comprising tetrazolo hydrazone derivatives according to the present invention will be described. These examples are provided only for illustrating the present invention and should not be construed as limiting the scope and spirit of the present invention.

Formulation Example 1

Powder Formulation

The tetrazolo hydrazone derivatives prepared in PREPARATION EXAMPLE 1 300 mg, lactose 100 mg and talc 10 mg are mixed and filled in the airtight pouch to prepare a powder formulation.

Formulation Example 2

Tablet Formulation

The tetrazolo hydrazone derivatives prepared in PREPARATION EXAMPLE 1 300 mg, cornstarch 100 mg, lactose 100 mg and magnesium stearate 2 mg are mixed and tablet pressed according to the conventional methods to prepare a tablet formulation.

Formulation Example 3

Capsule Formulation

The tetrazolo hydrazone derivatives prepared in PREPARATION EXAMPLE 1 50 mg, lactose 100 mg and magnesium stearate 2 mg are mixed and filled in gelatin capsule according to the conventional methods to prepare a capsule formulation.

Formulation Example 3

Injection Formulation

The tetrazolo hydrazone derivatives prepared in PREPARATION EXAMPLE 1 50 mg, distilled water for injection and pH regulator are mixed and filled in 2 mL ampule according to the conventional methods to prepare an injection formulation.

Formulation Example 3

Liquid Formulation

The tetrazolo hydrazone derivatives prepared in PREPARATION EXAMPLE 1 50 mg, Isomerized sugar 10 g and Mannitol 5 g are dissolved in purified water, added with an adequate amount of lemon flavor, mixed, and added with purified water to make 100 mL. The resulting liquid is filled in a brown bottle and sterilized according to the conventional methods to prepare a liquid formulation.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. Tetrazolo hydrazone derivatives represented by the following Formula 1 or pharmaceutically acceptable salts thereof:

[Formula 1]

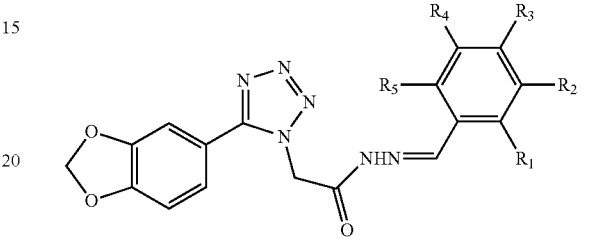

wherein, $R_1$, $R_2$, $R_3$, $R_4$ and $R_5$ are independently H, halogen, $NO_2$, $C_{1-4}$ alkyl, $C_{1-4}$ haloalkyl or $C_{1-4}$ alkoxy.

2. The tetrazolo hydrazone derivatives or pharmaceutically acceptable salts thereof according to claim 1, wherein $R_1$ is Cl, Br, or I; and, $R_2$, $R_3$, $R_4$ and $R_5$ are hydrogen.

3. The tetrazolo hydrazone derivatives or pharmaceutically acceptable salts thereof according to claim 1, wherein $R_1$, $R_2$, $R_3$, $R_4$ and $R_5$ are independently H or $NO_2$.

4. The tetrazolo hydrazone derivatives or pharmaceutically acceptable salts thereof according to claim 1, wherein $R_1$, $R_2$, $R_3$, $R_4$ and $R_5$ are independently H or methoxy.

5. The tetrazolo hydrazone derivatives or pharmaceutically acceptable salts thereof according to claim 1, wherein the tetrazolo hydrazone derivative is 2-[5-(1,3-Benzodioxol-5-yl)-1H-tetrazol-1-yl]-N'-[(2-chlorophenyl)methylidene]acetohydrazide, 2-[5-(1,3-Benzodioxol-5-yl)-1H-tetrazol-1-yl]-N'-[(3,4-dimethoxyphenyl)methylidene]acetohydrazide, 2-[5-(1,3-Benzodioxol-5-yl)-1H-tetrazol-1-yl]-N'-[(2-nitrophenyl)methylidene]acetohydrazide, 2-[5-(1,3-Benzodioxol-5-yl)-1H-tetrazol-1-yl]-N'-[(3-nitrophenyl)methylidene]acetohydrazide or 2-[5-(1,3-Benzodioxol-5-yl)-1H-tetrazol-1-yl]-N'-[(E)-(4-nitrophenyl)methylidene] acetohydrazide.

6. A pharmaceutical composition for treating cancer, which comprises the tetrazolo hydrazone derivatives or pharmaceutically acceptable salts thereof according to claim 1 as an active ingredient.

7. The pharmaceutical composition according to claim 6, wherein the cancer is solid cancer.

8. The pharmaceutical composition according to claim 7, wherein the solid cancer is Brain tumor, Low-grade astrocytoma, High-grade astrocytoma, Pituitary adenoma, Meningioma, CNS lymphoma, Oligodendroglioma, Craniopharyngioma, Ependymoma, Brain stem tumor, Head & Neck tumor, Larygeal cancer, Oropgaryngeal cancer, Nasal cavity/PNS tumor, Nasopharyngeal tumor, Salivary gland tumor, Hypopharyngeal cancer, Thyroid cancer, Oral cavity tumor, Chest Tumor, Small cell lung cancer, Non small cell lung cancer, Thymoma, Mediastinal tumor, Esophageal cancer, Breast cancer, Male breast cancer, Abdomen-pelvis tumor, Stomach cancer, Hepatoma, Gall bladder cancer, Billiary tract tumor, pancreatic cancer, Small intestinal tumor, Large intestinal tumor, Anal cancer, Bladder cancer, Renal cell carcinoma, Male genital cancer, Penile cancer, Prostatic cancer, Female genital cancer, Cervix cancer, Endometrial cancer, Ovarian cancer, Uterine sarcoma, Vaginal cancer, Vulva cancer, Urethral cancer or Skin cancer.

9. A method for treating cancer, which comprises administering to the subject an effective amount of tetrazolo hydrazone derivatives or pharmaceutically acceptable salts thereof according to claim 1.

* * * * *